United States Patent [19]

Klawitter et al.

[11] 4,000,525
[45] Jan. 4, 1977

[54] CERAMIC PROSTHETIC IMPLANT SUITABLE FOR A KNEE JOINT PLATEAU

[75] Inventors: Jerome J. Klawitter, Clemson, S.C.; Nazir A. Bhatti, Augusta, Ga.

[73] Assignee: The United States of America as represented by the Secretary of the Navy, Washington, D.C.

[22] Filed: Aug. 21, 1975

[21] Appl. No.: 606,630

[52] U.S. Cl. .................................. 3/1.911; 3/1.91; 128/92 C; 264/44; 106/40 R
[51] Int. Cl.² ......................................... A61F 1/24
[58] Field of Search ............................ 3/1.9–1.913, 3/1; 128/92 C, 92 CA; 32/10 A; 106/39.5, 40 R, 41

[56] References Cited

UNITED STATES PATENTS

| | | | |
|---|---|---|---|
| 3,314,420 | 4/1967 | Smith et al. | 128/92 C |
| 3,707,006 | 12/1972 | Bokros et al. | 3/1 |
| 3,728,742 | 4/1973 | Averill et al. | 3/1.911 |
| 3,924,275 | 12/1975 | Heimke et al. | 3/1.912 |

FOREIGN PATENTS OR APPLICATIONS

| | | | |
|---|---|---|---|
| 2,400,134 | 7/1974 | Germany | 3/1.9 |
| 1,334,584 | 10/1973 | United Kingdom | 3/1.912 |

OTHER PUBLICATIONS

"Ceramics In Surgery" by R. P. Welsh et al., *Journal Biomedical Materials Symposium*, vol. 2 (part 1), pp. 231–249, 1972.

"Biological Activity And Histocompatiblity of Dense $Al_2O_3$/MgO Ceramic Implants in Rats" by P. Griss et al., *J. Biomedical Material Research Symposium*, No. 4, pp. 453–462, 1973.

"Experimental Analysis of Ceramic–Tissue Interactions. A Morphologic, Fluoroscenseoptic, and Radiographic Study on Dense Alumina Oxide Ceramic in Various Animals" by Peter Griss et al., *J. Biomedical Materials Research Symposium*, No. 5, (part 1), pp. 39–48, 1974.

"Effects of Stress on Tissue Ingrowth into Porous Alumina Oxide" by S. F. Hulbert et al., *J. Biomedical Materials Research Symposium*, No. 5 (part 1), pp. 85–97, 1974.

*Primary Examiner*—Ronald L. Frinks
*Attorney, Agent, or Firm*—R. Sciascia; R. Beers; S. Sheinbein

[57] ABSTRACT

A ceramic prosthesis of high aluminum oxide suitable for the tibial plateau of a knee joint with the superior (upper) portion of the prosthesis being of a high density $AL_2O_3$ having a very low porosity and the inferior (lower) portion being of high density $AL_2O_3$ having a high degree of porosity capable of accepting bone growth.

7 Claims, 1 Drawing Figure

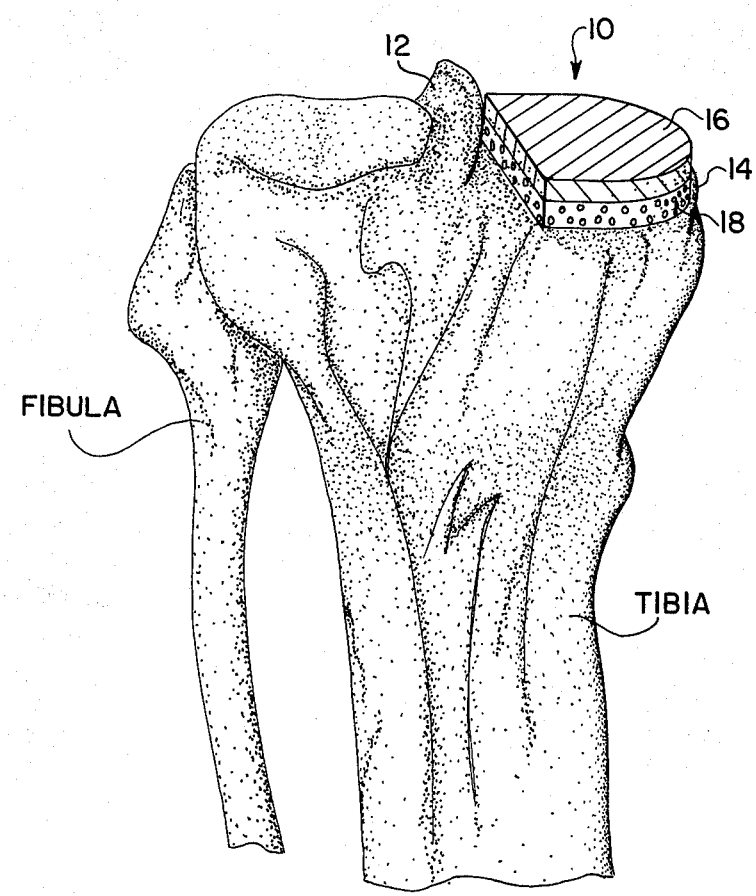

CERAMIC PROSTHETIC IMPLANT SUITABLE FOR A KNEE JOINT PLATEAU

BACKGROUND OF THE INVENTION

Prior methods used in the reconstruction of tibial plateaus have involved the application of solid metal prosthesis. These solid metallic tibial plateau devices have had limited use due to the lack of adequate chemical stabilization. The inability to bond the solid metallic devices permanently to bone results in mobility which has limited the long term usefulness of the metallic implants.

Metallic implants are subject to corrosion and may cause an adverse tissue reaction if corrosion takes place.

OBJECTS OF THE INVENTION

An object of the invention is to enable the surgical reconstruction of the tibial plateau of the knee joint which has been destroyed by disease or trauma by means of an improved and highly effective prosthetic implant.

Another object is to provide a prosthetic implant made completely of a ceramic composition material which has long term usefulness, is highly nonreactive and very compatible, shows chemical stability, non-toxicity, and has a porous portion which will inhibit any osteoid or other tissue seam where the mineralized bone ingrowth juxtaposes the porous portion when implanted in a body.

Another object is to provide a prosthesis of such structure and high aluminum oxide content composition useful for the reconstruction of the tibial plateau of the knee joint which can be permanently bonded to living bone by favorably affecting bone tissue ingrowth into the pores of the implant.

Other objects, advantages, and novel features of the present invention will become apparent from the following detailed description of the invention when considered in conjunction with the accompanying drawings.

BRIEF SUMMARY OF INVENTION

The invention consists of a tibial plateau prosthesis constructed of aluminum oxide ($AL_2O_3$). The superior portion of the implant is constructed of a high density aluminum oxide which will act as the articulating surface and the inferior portion of the implant will be constructed of a porous aluminum oxide capable of accepting bone ingrowth in order to stabilize the device in the tibia. The high density aluminum oxide has a porosity preferably not greater than 1 percent and the porous aluminum oxide has a porosity of approximately 50 percent with pore sizes between 350 and 500 micrometers in diameter. The pores are highly interconnecting. The implant is shaped so that the smooth articulating surface of the dense superior portion duplicates the functional geometry of the natural surface with which the femoral condyle articulates. The high density aluminum oxide material is approximately 1 centimeter thick and the porous inferior portion has a minimum thickness of 1 centimeter. The overall thickness of the implant can be varied by increasing the thickness of the porous aluminum oxide inferior portion. The anterior-posterior and lateral-medial dimensions of the implant are such that when it is installed in the tibia a border of anterior, medial or lateral and posterior bone will remain and provide initial stabilization while bone ingrowth takes place. The inertness of this material helps eliminate adverse host tissue reaction.

BRIEF DESCRIPTION OF DRAWING

The single FIGURE of the drawing shows how the prosthesis of the invention is used on a human knee joint to surgically reconstruct the tibial plateau. A border of anterior medial or lateral and posterior bone is shown remaining in place to provide initial stabilization.

DETAILED DESCRIPTION

The drawing shows the fibula and tibia bones connected together at a human knee joint with the prosthesis 10 of the invention in the medial plateau of the tibia. Borders 12 and 14 of the bone remain in place to initially stabilize the implant prosthesis 10 in proper location on the plateau.

The implant 10 is made of a superior dense portion 16 of high aluminum oxide material laminated to an inferior highly porous portion 18 of high aluminum oxide material.

The high density superior portion may be 1 centimeter thick while the porous inferior portion has a minimum thickness of 1 centimeter. The bottom surface of porous portion 18 is planar and engages the flat bone surface of the tibial plateau while its sides engage the borders 12 and 14. The high density aluminum oxide superior portion has a porosity preferably not greater than 1 percent while the inferior porous aluminum oxide portion has a porosity in the range between 40–60%, such as approximately 50% with highly interconnecting pores whose pore sizes are between 350 and 500 microns in diameter.

The oxide composition of the high aluminum oxide ceramic material is given in the following table. The raw materials used to produce this material are alpha aluminum oxide, kaolin clay, talc and $C_aCO_3$. The aluminum oxide raw material possessed an average grain size of approximately 5 micrometers.

Table

| Oxide Composition of High Aluminum Oxide Material | |
|---|---|
| Oxide | Weight Percent |
| Alpha $Al_2O_3$ | 96 |
| $SiO_2$ | 2.7 |
| MgO | 1.0 |
| CaO | 0.2 |
| $Na_2O$ | 0.1 |

In obtaining the tibial plateau prosthesis of the invention the following process to obtain controlled pore size by a foaming procedure was employed along the lines described in copending application of J. J. Klawitter, Ser. No. 577,525, filed May 14, 1975 one of the joint inventors hereof.

Three hundred grams of the raw materials were weighed and mixed with 135 cc of a 3.5 weight percent polyvinyl alcohol solution to produce a viscous slip. The foaming agent (30% $H_2O_2$) was then added to the slip and thoroughly mixed. A catalyst was then added to the slip to control the decomposition of the foaming agent. The catalyst used to decompose the $H_2O_2$ was two drops of whole citrated blood per 300 gram powder batch. The catalyst was mixed into the slip and within 30 seconds the slip infiltrated into a high porosity sponge which is introduced into the foaming procedure, where it was allowed to decompose. The sponge material used was commercially available from the Foam Division of the Scott Paper Company, Chester, Pa. The foam material is called Scott Industrial Foam and is a reticulated, fully "open-pore," flexible ester type of polyurethane foam (a fully reticulated polymeric sponge). It is characterized by a three-dimensional skeletal structure of strands which provide a constant 97 percent of void space and a very high degree of permeability. The pore size of the sponge material is characterized by the number of pores per linear inch (ppi) and is available over a range of 10 to 100 ppi.

Control over the pore size of the final ceramic material product was achieved by varying the pore per linear inch size of the high porosity fully reticulated polymeric sponge. A 60 ppi sponge was found to produce a highly interconnected pore structure with pore diameters of approximately 300–400 micrometers. Stated another way, the geometry of the polymeric sponge structure controlled the size, shape and distribution of the gas bubbles generated during foaming and in this way controlled the pore structure.

The percent porosity was controlled by varying the amount of foaming agent added to the viscous slip. The relationship between the volume of 30% $H_2O_2$ solution was added to the 300 gram powder batch and the porosity of the resulting aluminum oxide material was found to be approximately linear between 0.5 cc of 30% $H_2O_2$ which produced an approximately 40% porosity and 3.0 cc of 30% $H_2O_2$ which produced a final porosity of approximately 60 %. It should be noted that the relationship between the amount of foaming agent and the percent porosity in the resulting ceramic was dependent on the actual concentration of $H_2O_2$ solution and the rate of decomposition. After the foaming operation the material was allowed to dry at room temperature.

The porous and dense portions 18 and 16 respectively, result from two fabrication processes and these are subsequently united. The porous material is produced as outlined above. The dense non-porous material is produced from the same high raw aluminum oxide material composition using a dry pressing operation with no foaming procedures. The powders are merely compacted at a pressure of 5000 psi to form the dense layer. The porous and non-porous portions are then laminated before they are fitted using an aqueous slurry of the same high aluminum oxide material composition. The lamination is accomplished by grinding the porous material (in the unfired state) to produce a planar surface. The non-porous and porous materials are then laminated at the planar surface using the slurry. The laminate is then dried and fired to 1600° C for 4 hours. This is the only firing or sintering step in making the laminated implant.

The actual shape and dimension of the implant must conform to the anatomy of the knee and the type of reconstruction desired. Since the material is very hard and not suited to shaping at the time of surgery, a number of different shapes may have to be available to suit a specific application to a particular patient. Variations in the shape of the articulating surface and variations in the overall thickness of the device would be required and can be done by using a precision diamond cutting saw.

There has been described a novel ceramic tibial plateau prosthesis of controlled pore size comprising a highly dense superior portion of high aluminum oxide and a highly porous inferior portion of high aluminum oxide, both laminated together, and the method of fabricating the laminated completed structure. This prosthesis is characterized by biocompatibility evidenced by no abnormal tissue reactions to the aluminum oxide, no signs of abnormal carcinogenic, allergenic, immunologic or inflammatory response. The materials' chemical stability and non-toxicity are supported by the lack of any osteoid as other tissue seam where the mineralized bone juxtaposed the aluminum oxide. The implant of the invention demonstrates that with habitual weight bearing, undamaged musculature, and normal vascularity there is excellent mechanical compatibility with both cortical bone and surrounding soft tissues.

Obviously, many modifications and variations of the present invention are possible in light of the above teachings. It is therefore to be understood that, within the scope of the appended claims, the invention may be practice otherwise than as specifically described.

What is claimed is:

1. A prosthesis comprising a porous layer having approximately 96 weight percent of aluminum oxide and a porosity in the range of 40–60% with interconnecting pores, laminated to a dense layer of approximately 96 weight percent of aluminum oxide having a porosity of not greater than 1 percent.

2. A prosthesis as defined in claim 1 wherein said porous layer has an exposed planar surface and pore diameters in the approximate range of 300–500 micrometers, said dense layer having a smooth outer surface.

3. A prosthesis according to claim 2 wherein said porous layer has a minimum thickness of 1 centimeter and said dense layer has a thickness of 1 centimeter.

4. A prosthesis according to claim 1 wherein the oxide composition of the aluminum oxide material is as follows

| Oxide | Weight Percent |
| --- | --- |
| Alpha $AL_2O_3$ | 96 |
| $SiO_2$ | 2.7 |
| MgO | 1.0 |
| CaO | 0.2 |
| $Na_2O$ | 0.1 |

5. A prosthesis designed as an implant for the tibial plateau of a knee joint comprising:
 a. a first dense layer of high aluminum oxide ceramic material having a smooth outer surface to articulate with the femoral condyle;
 b. a second porous layer of high aluminum oxide ceramic material laminated to said first layer and having a planar surface adapted to engage said tibial plateau,
 c. said dense layer having a porosity not greater than 1 percent; and
 d. said porous layer having a porosity in the range of 40–60 percent with interconnecting pores of controlled pore size.

6. A prosthesis according to claim 5 wherein the aluminum oxide content of each of said layers is approximately 96 percent, the pore diameters of said porous layer being in the range of 350–500 micrometers.

7. A completely ceramic prosthesis for use as a bone implant in a joint comprising:
 a. a layer of high aluminum oxide material having a porosity in the range of 40–60% with interconnecting pores;
 b. said layer having a planar surface; and
 c. a dense layer of high aluminum oxide material having a porosity not greater than 1% laminated to said first porous layer at said planar surface;
 d. the outer surface of said dense layer being smooth to act as an articulate surface in said joint.

* * * * *